(12) United States Patent
Sims et al.

(10) Patent No.: US 11,382,685 B2
(45) Date of Patent: Jul. 12, 2022

(54) ELECTROSURGICAL FORCEPS

(71) Applicant: COVIDIEN LP, Mansfield, MA (US)

(72) Inventors: Grant T. Sims, Boulder, CO (US);
Daniel W. Mercier, Erie, CO (US);
Craig V. Krastins, Arvada, CO (US);
Jennifer L. Rich, Parker, CO (US);
Kelley D. Goodman, Erie, CO (US)

(73) Assignee: Covidien LP, Mansfield, MA (US)

( * ) Notice: Subject to any disclaimer, the term of this patent is extended or adjusted under 35 U.S.C. 154(b) by 450 days.

(21) Appl. No.: 16/454,133

(22) Filed: Jun. 27, 2019

(65) Prior Publication Data
US 2020/0405374 A1 Dec. 31, 2020

(51) Int. Cl.
A61B 17/29 (2006.01)
A61B 18/14 (2006.01)
A61B 17/00 (2006.01)
A61B 18/00 (2006.01)

(52) U.S. Cl.
CPC ...... A61B 18/1442 (2013.01); A61B 2017/00862 (2013.01); A61B 2017/2947 (2013.01); A61B 2018/0063 (2013.01)

(58) Field of Classification Search
CPC ............ A61B 17/2816; A61B 18/1442; A61B 2017/00862; A61B 2017/2947; A61B 2018/0063; A61B 2018/00916; A61B 2018/0094; A61B 2018/1455; A61B 2090/032
USPC ...................... 606/51–52, 142, 169, 205–207
See application file for complete search history.

(56) References Cited

U.S. PATENT DOCUMENTS

| | | | |
|---|---|---|---|
| 5,745,997 A | 5/1998 | Berg et al. | |
| 8,828,023 B2 | 9/2014 | Neff et al. | |
| 9,005,200 B2 | 4/2015 | Roy et al. | |
| 2003/0199869 A1* | 10/2003 | Johnson | A61B 18/1445 606/50 |
| 2006/0217697 A1 | 9/2006 | Lau et al. | |
| 2013/0018372 A1* | 1/2013 | Sims | A61B 18/1442 606/45 |
| 2016/0175033 A1 | 6/2016 | Le | |
| 2017/0196648 A1 | 7/2017 | Ward et al. | |
| 2017/0348045 A1 | 12/2017 | Brennan | |
| 2018/0325580 A1 | 11/2018 | Sims et al. | |

FOREIGN PATENT DOCUMENTS

| | | |
|---|---|---|
| EP | 2392271 A1 | 12/2011 |
| WO | 2007047380 A2 | 4/2007 |
| WO | 2016025132 A1 | 2/2016 |
| WO | 2016028980 A1 | 2/2016 |

OTHER PUBLICATIONS

European Search Report dated Nov. 12, 2020, issued in corresponding EP Appln. No. 20182639, 8 pages.

* cited by examiner

Primary Examiner — Khadijeh A Vahdat

(57) ABSTRACT

An electrosurgical forceps includes a pair of first and second shaft members pivotably coupled to one another, an end effector assembly coupled to the pair of first and second shaft members, and a resilient, compressible pivot assembly pivotably coupling the first and second shaft members to one another.

20 Claims, 4 Drawing Sheets

ELECTROSURGICAL FORCEPS

BACKGROUND

A surgical forceps is a plier-like instrument which relies on mechanical action between its jaws to grasp tissue. Electrosurgical forceps utilize both mechanical clamping action and electrical energy to treat tissue, e.g., coagulate, cauterize, and/or seal tissue.

Typically, once tissue is treated, the surgeon has to accurately sever the treated tissue. Accordingly, many electrosurgical forceps have been designed which incorporate a knife configured to effectively sever tissue after treating the tissue.

SUMMARY

As used herein, the term "distal" refers to the portion that is being described which is further from a surgeon, while the term "proximal" refers to the portion that is being described which is closer to a surgeon. Further, to the extent consistent, any of the aspects described herein may be used in conjunction with any or all of the other aspects described herein.

As used herein, the terms parallel and perpendicular are understood to include relative configurations that are substantially parallel and substantially perpendicular up to about +/−10 degrees from true parallel and true perpendicular.

An electrosurgical forceps provided in accordance with aspects of the present disclosure includes first and second shaft members, first and second jaw members, a pivot pin, and a resilient pivot member. The first shaft member has a distal end portion pivotably coupled to a distal end portion of the first shaft member about the pivot pin. The first jaw member is coupled to and extends from the distal end portion of the first shaft member, and the second jaw member is coupled to and extends from the distal end portion of the second shaft member. The first and second jaw members are configured to move between an open configuration and a closed configuration in response to pivoting of the first and second shaft members. The resilient pivot member is associated with the pivot pin and configured to assure a sealing pressure between the first and second jaw members to promote tissue sealing within a range of about 3 kg/cm² to about 16 kg/cm².

In aspects, the resilient pivot member may be configured to compress between the distal end portions of the first and second shaft members in response to a threshold force and yield the sealing pressure between jaw members within the range.

In aspects, the pivot pin may extend through an opening defined through the distal end portion of each of the first and second shaft members.

In aspects, the resilient pivot member may enshroud the pivot pin.

In aspects, the resilient pivot member may be more resilient than the pivot pin.

In aspects, the pivot pin may be fabricated from a metal.

In aspects, the pivot pin may be fabricated from steel.

In aspects, the resilient pivot member may be fabricated from a rubber or a plastic.

In aspects, the resilient pivot member may be configured to compress about the pivot pin in response to a threshold force applied by the distal end portions of the first and second shaft members.

In aspects, the pivot pin may be fabricated from a rigid material and the resilient pivot member may be fabricated from a soft material.

In accordance with another aspect of the disclosure, an electrosurgical forceps is provided and includes a pair of first and second shaft members pivotably coupled to one another, an end effector assembly coupled to the pair of first and second shaft members, and a pivot assembly pivotably coupling the first and second shaft members to one another. The end effector assembly is configured to move between an open configuration and a closed configuration in response to pivoting of the first and second shaft members. The pivot assembly includes a rigid pivot pin, and a resilient and compressible sheath disposed about the pivot pin.

In aspects, each of the first and second shaft members may have an opening defined laterally therethrough. The pivot assembly may be received in the openings.

In aspects, the sheath may be configured to compress between the first and second shaft members in response to a threshold force.

In aspects, the pivot pin may be fabricated from a metal.

In aspects, the pivot pin may be fabricated from steel.

In aspects, the sheath may be fabricated from a rubber or a plastic.

In aspects, the sheath may be configured to compress about the pivot pin in response to a threshold force applied by the first and second shaft members.

In aspects, the second shaft member may be rigid along a length thereof.

In aspects, the first and second shaft members may be configured to resist flexing during approximation of the end effector assembly.

In aspects, the first shaft member may have a proximal end portion, and the second shaft member may have a proximal end portion supporting an activation switch configured to be engaged by the proximal end portion of the first shaft member upon approximation of the proximal end portions of the first and second shaft members about the pivot assembly.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
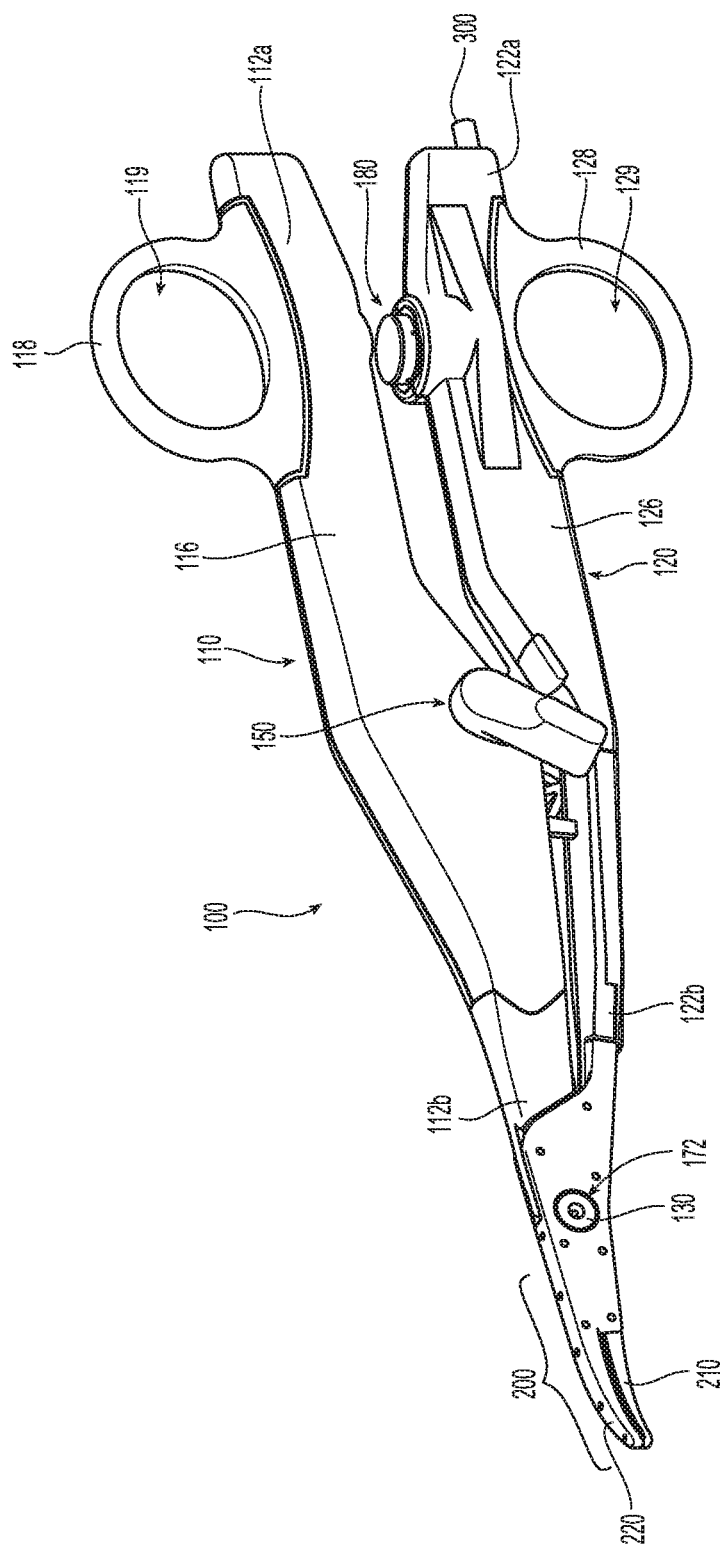
FIG. 1 is a side, perspective view of an electrosurgical forceps provided in accordance with aspects of the present disclosure.
Figure 2:
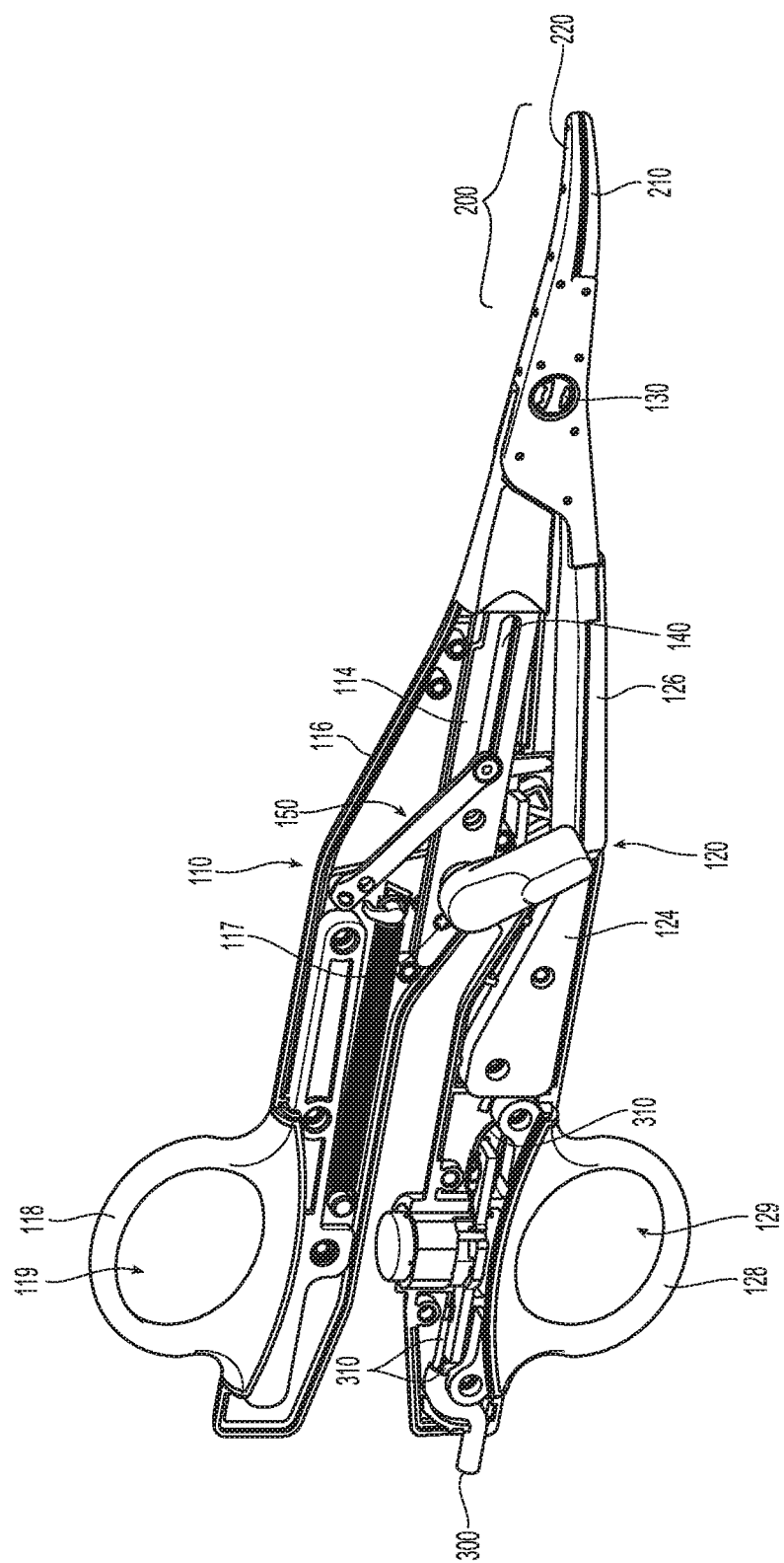
FIG. 2 is a perspective view from one side of the forceps of FIG. 1 with portions of outer housings of first and second shaft members removed to illustrate the internal components therein.

Referring to FIGS. 1 and 2, a forceps 100 provided in accordance with the present disclosure generally includes first and second shaft members 110, 120 and an end effector assembly 200. Shaft members 110, 120 each have a proximal end portion 112a, 122a and a distal end portion 112b, 122b, respectively. End effector assembly 200 includes first and second jaw members 210, 220 extending from distal end portions 112b, 122b of first and second shaft members 110, 120, respectively. Forceps 100 further includes a pivot assembly 130 pivotably coupling first and second shaft members 110, 120 with one another, a knife 140, a knife deployment mechanism 150 for selectively deploying knife 140, and a switch assembly 180 for enabling the selective supply of electrosurgical energy to end effector assembly 200. An electrosurgical cable 300 electrically couples forceps 100 to a source of energy (not shown), e.g., an electrosurgical generator, to enable the supply of electrosurgical energy to jaw members 210, 220 of end effector assembly 200 upon activation of switch assembly 180.

Each shaft member 110, 120 includes an inner frame 114, 124, an outer housing 116, 126 surrounding at least a portion of the respective inner frame 114, 124, and a handle 118, 128 engaged with the respective outer housing 116, 126 towards proximal end portions 112a, 122a of first and second shaft members 110, 120, respectively. Inner frame 124 of second shaft member 120 and inner frame 114 of first shaft member 110 are pivotably coupled to one another via pivot assembly 130 such that shaft members 110, 120 are movable relative to one another between spaced-apart and approximated positions to thereby pivot jaw members 210, 220 relative to one another between open and closed positions.

Outer housings 116, 126 of first and second shaft members 110, 120 enclose and/or operably support the internal components disposed within first and second shaft members 110, 120. More specifically, outer housing 116 of first shaft member 110 encloses and supports at least a portion of inner frame 114 and knife deployment mechanism 150, while outer housing 126 of shaft member 120 receives electrosurgical cable 300 and encloses and supports at least a portion of inner frame 124, switch assembly 180, and the lead wires 310 of electrosurgical cable 300. Handles 118, 128 are engaged with outer housings 116, 126 towards proximal end portions 112a, 112b of first and second shaft members 110, 120 and extend outwardly from first and second shaft members 110, 120. Handles 118, 128 define finger holes 119, 129 configured to facilitate grasping and manipulating shaft members 110, 120. The first and second shaft members 110, 120 may each be rigid, such that they resist flexing during approximation of the end effector assembly 200.

Figure 3A:
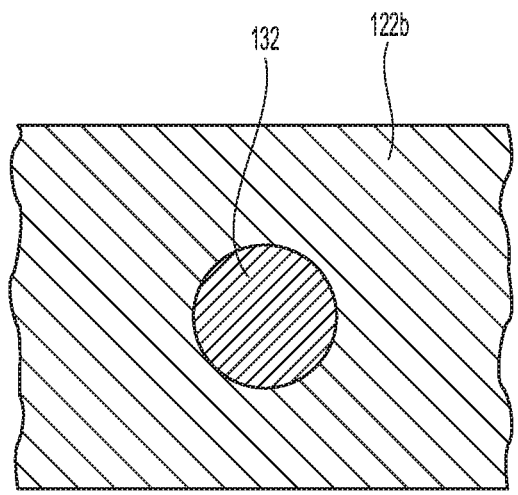
FIG. 3A is an enlarged, side view of a first side of a pivot assembly of the electrosurgical forceps of FIG. 1.
Figure 3B:
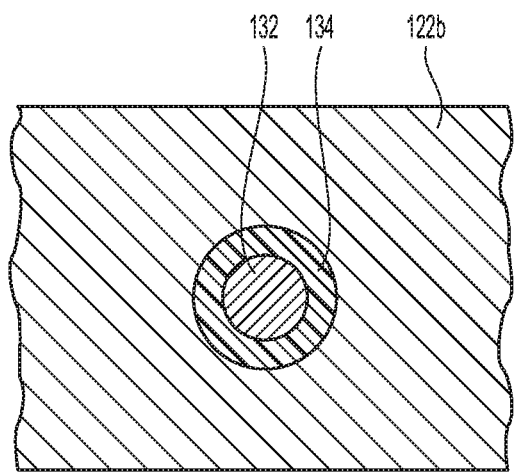
FIG. 3B is an enlarged, side view of a second side of the pivot assembly of FIG. 3A.
Figure 4:
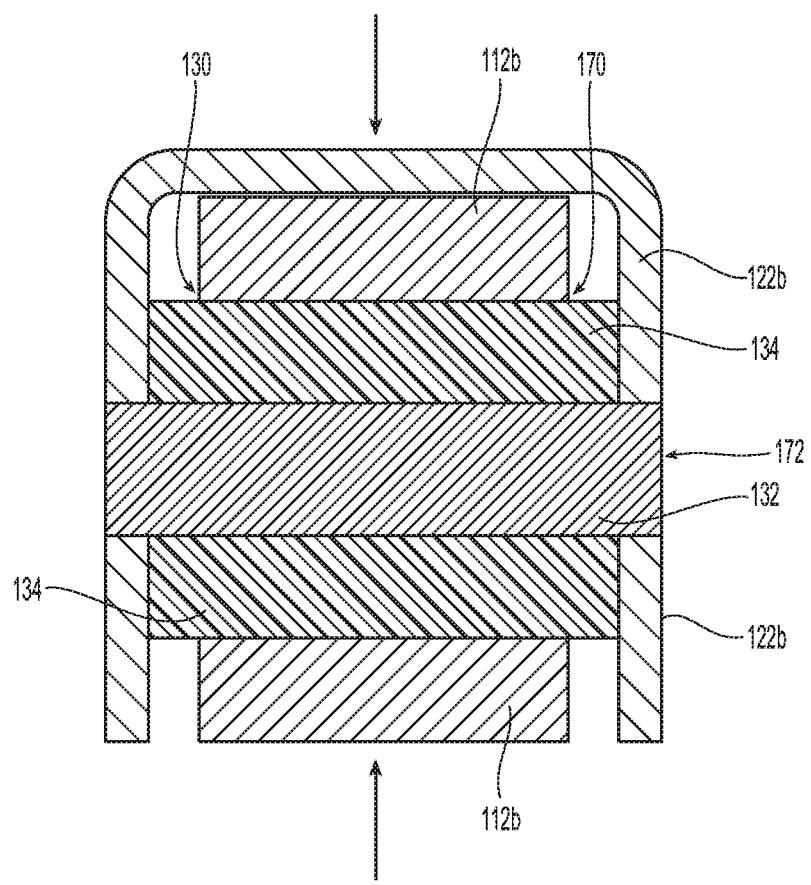
FIG. 4 is a transverse cross-sectional view of the pivot assembly of FIG. 3A shown received in the first and second shaft members.

FIGS. 3A, 3B, and 4 illustrate the pivot assembly 130 for pivotably coupling the distal end portions 112b, 122b of the first and second shaft members 110, 120 to one another. The distal end portion 112b, 122b of each of the first and second shaft members 110, 120 defines an opening or channel 170, 172 extending laterally (e.g., transversely relative to a longitudinal axis of the respective shaft member 110, 120) therethrough. The pivot assembly 130 is received in the openings 170, 172 and is non-rotationally fixed therein. In some aspects, the pivot assembly 130 may be configured to rotate within the openings 170, 172.

The pivot assembly 130 includes a pivot pin 132 and a pivot member 134 disposed about the outer periphery of the pivot pin 132. The pivot pin 132 may have a generally cylindrical configuration and the pivot member 134 may be a hollow sheath that enshrouds the pivot pin 132. In aspects, the pivot member 134 may be a coating. The pivot pin 132 is fabricated from a rigid material that resists compression during pivoting of the shaft members 110, 120 thereabout. For example, the pivot pin 132 may be fabricated from a metal (e.g., steel or surgical stainless steel), a ceramic, rigid plastic, etc. The pivot member 134 is fabricated from a resilient and compressible material configured to compress in response to an application of a threshold force from the first and second shaft members 110, 120. For example, the pivot member 134 may be fabricated from a rubber or plastic, such as, for example, polyurethane. In some aspects, the pivot member 134 may be a biasing member, such as, for example, a spring. The pivot member 134 may be electrically insulated to electrically isolate the first and second jaw members 210, 220. The pivot member 134 may be configured to resist wear, provide lubrication, minimize galling, etc.

In use, tissue may be positioned between the jaw members 210, 220 of the end effector assembly 200 followed by an approximation of the proximal end portions 112a, 122a of first and second shaft members 110, 120. Approximation of the proximal end portions 112a, 122a of the first and second shaft members 110, 120 pivot the distal end portions 112b, 122b of the first and second shaft members 110, 120 about the pivot assembly 130 to approximate the jaw members 210, 220 of the end effector assembly 200.

With the end effector assembly 200 in the closed configuration about the tissue, a threshold actuation force is applied to the pivot assembly 130 via the distal end portions 112b, 122b of the first and second shaft members 110, 120. The threshold actuation force is sufficient to compress the pivot member 134 of the pivot assembly 130 radially inward toward the pivot pin 132, thereby causing the end effector assembly 200 to apply a predetermined, constant clamping pressure on the tissue. Eventually, the proximal end portion 112a of the first shaft member 110 contacts the activation switch 180 (FIG. 1) to deliver electrosurgical energy to the tissue. Pivot member 134 may be fabricated from a resilient material or arranged in such a fashion about the pivot pin 132 to assure a consistent pressure between jaw members during approximation of tissue with a range of about 3 kg/cm$^2$ to about 16 kg/cm$^2$ to facilitate sealing tissue disposed therebetween. For example, the material of the pivot member 134 may be made from a particular urethane that coupled with the forces applied by the user on the handles 118, 128 yields a closure pressure within the above-noted sealing range. Alternatively or in combination, the pivot member 134 may be positioned about the pivot pin 132 or have a particular thickness or shape that assures a consistent closure pressure within the above-noted sealing range.

In aspects, the pivot member 134 may be keyed to the distal end portion 112b, 122b of each of the first and second shaft members 110, 120. The pivot pin 132 may be rotatable within the pivot member 134 and/or may grip the inner frames and/or outer housings 114, 116, 124, 126. The pivot member 134 may have a varied thickness along a direction of compression so as to control deflection of the jaw members 210, 220. In aspects, the pivot member 134 may have a width extending the entire width of the openings 170, 172 of the distal end portion 112b, 122b of each of the first and second shaft members 110, 120. The pivot member 134 may have a different durometer or the same durometer throughout. For example, the lateral ends of the pivot member 134 may have a different durometer than its interior, or the upper half of the pivot member 134 may have a different durometer than the lower half thereof.

In another embodiment, the pivot assembly may include a resilient core or pin, a flexible outer shell or tube disposed about the pin, and a resilient cylinder disposed about the outer tube. In aspects, the inner pin and/or the outer tube may be rigid and/or metallic rather than being resilient.

For additional description of various components and manners of operating forceps 100 of the present disclosure, reference may be made to U.S. Patent Application Publication No. 2018/0325580, the entire contents of which are incorporated by reference herein.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Pat. No. 8,828,023, the entire contents of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An electrosurgical forceps, comprising:
    a first shaft member;
    a second shaft member having a distal end portion pivotably coupled to a distal end portion of the first shaft member about a pivot pin;
    a first jaw member coupled to and extending from the distal end portion of the first shaft member;
    a second jaw member coupled to and extending from the distal end portion of the second shaft member, the first and second jaw members configured to move between an open configuration and a closed configuration in response to pivoting of the first and second shaft members; and
    a resilient pivot member associated with the pivot pin and configured to assure a sealing pressure between the first and second jaw members to promote tissue sealing within a range of about 3 kg/cm2 to about 16 kg/cm2, wherein the resilient pivot member extends through the distal end portion of the first and second shaft members and around at least a central region of the pivot pin.

2. The electrosurgical forceps according to claim 1, wherein the resilient pivot member is configured to compress between the distal end portions of the first and second shaft members in response to a threshold force and yield the sealing pressure between the first and second jaw members within the range.

3. The electrosurgical forceps according to claim 1, wherein the pivot pin extends through an opening defined through the distal end portion of each of the first and second shaft members.

4. The electrosurgical forceps according to claim 1, wherein the resilient pivot member enshrouds the pivot pin.

5. The electrosurgical forceps according to claim 1, wherein the resilient pivot member is more resilient than the pivot pin.

6. The electrosurgical forceps according to claim 1, wherein the pivot pin is fabricated from a metal.

7. The electrosurgical forceps according to claim 1, wherein the pivot pin is fabricated from steel.

8. The electrosurgical forceps according to claim 1, wherein the resilient pivot member is fabricated from a rubber or a plastic.

9. The electrosurgical forceps according to claim 1, wherein the resilient pivot member is configured to compress about the pivot pin in response to a threshold force applied by the distal end portions of the first and second shaft members.

10. The electrosurgical forceps according to claim 1, wherein the pivot pin is fabricated from a rigid material and the resilient pivot member is fabricated from a soft material.

11. An electrosurgical forceps, comprising:
    a pair of first and second shaft members each having a distal end portion pivotably coupled to one another;
    an end effector assembly coupled to the pair of first and second shaft members and configured to move between an open configuration and a closed configuration in response to pivoting of the first and second shaft members; and
    a pivot assembly pivotably coupling the first and second shaft members to one another, the pivot assembly including:
    a rigid pivot pin; and
    a resilient and compressible sheath disposed about at least a central region of the pivot pin and extending through the distal end portion of the first and second shaft members.

12. The electrosurgical forceps according to claim 11, wherein each of the first and second shaft members has an opening defined laterally therethrough, the pivot assembly received in the openings.

13. The electrosurgical forceps according to claim 11, wherein the sheath is configured to compress between the first and second shaft members in response to a threshold force.

14. The electrosurgical forceps according to claim 11, wherein the pivot pin is fabricated from a metal.

15. The electrosurgical forceps according to claim 14, wherein the pivot pin is fabricated from steel.

16. The electrosurgical forceps according to claim 15, wherein the sheath is fabricated from a rubber or a plastic.

17. The electrosurgical forceps according to claim 11, wherein the sheath is configured to compress about the pivot pin in response to a threshold force applied by the first and second shaft members.

18. The electrosurgical forceps according to claim 11, wherein the second shaft member is rigid along a length thereof.

19. The electrosurgical forceps according to claim 18, wherein the first and second shaft members are configured to resist flexing during approximation of the end effector assembly.

20. The electrosurgical forceps according to claim 11, wherein the first shaft member has a proximal end portion, and the second shaft member has a proximal end portion supporting an activation switch configured to be engaged by the proximal end portion of the first shaft member upon approximation of the proximal end portions of the first and second shaft members about the pivot assembly.

\* \* \* \* \*